United States Patent [19]
Russ et al.

[11] Patent Number: 5,585,489
[45] Date of Patent: Dec. 17, 1996

[54] WATER-SOLUBLE TRIPHENDIOXAZINE COMPOUNDS AND THEIR USE AS DYESTUFFS

[75] Inventors: Werner H. Russ, Flörsheim; Christian Schumacher, Frankfurt, both of Germany

[73] Assignee: Hoechst AG, Germany

[21] Appl. No.: 434,682

[22] Filed: May 4, 1995

[30]　　Foreign Application Priority Data

May 4, 1994　[DE]　Germany .................. 44 15 692.8

[51] Int. Cl.$^6$ .................. C07D 498/04; C09B 19/00; C09B 62/04; C09B 62/503
[52] U.S. Cl. .................. 544/76; 544/77; 8/404; 8/506; 8/549
[58] Field of Search .................. 544/76, 77; 8/404, 8/506, 549

[56]　　　　References Cited

U.S. PATENT DOCUMENTS

| | | | |
|---|---|---|---|
| 4,604,459 | 8/1986 | Jager | 544/76 |
| 4,841,049 | 6/1989 | Seitz | 544/76 |

FOREIGN PATENT DOCUMENTS

| | | |
|---|---|---|
| 0070807 | 1/1983 | European Pat. Off. . |
| 0074928 | 3/1983 | European Pat. Off. . |
| 0170838 | 2/1986 | European Pat. Off. . |
| 629667 | 12/1994 | European Pat. Off. . |
| 1576237 | 10/1980 | United Kingdom . |

*Primary Examiner*—Philip I. Datlow
*Attorney, Agent, or Firm*—Connolly & Hutz

[57]　　　　ABSTRACT

Triphendioxazine compounds corresponding to the formula (1)

in which Z is a radical of the formula (2)

in which $Y^1$ and $Y^2$ each vinyl β-hydroxyethyl or an ethyl radical which contains a substituent which can be eliminated under alkaline conditions in the β-position, and in which $Y^1$ and $Y^2$ are not simultaneously β-hydroxyethyl, $W^1$ and $W^2$ are both allyene having 2 to 6 carbon atoms, A is a covalent bond of a group of the formula —$B^1$—N($R^3$)—, in which $R^3$ has one of the meanings of $R^1$ and $B^1$ is an aliphatic or aromatic bridge member, and in which the group —N($R^1$)—$B^1$—N($R^3$)— can also be in total a bivalent saturated heterocyclic radical, and $Z^0$ is hydrogen or a group of the formula (4)

in which $A^0$ is a covalent bond or a radical or the formula —N($R^4$)—$B^2$— having the meaning corresponding to the above formula —$B^1$(N$R^3$)— are described. The triphendioxazine compounds of the formula (1) are used as fiber-reactive dyestuffs for dyeing material containing hydroxy, amino and/or carboxamide groups.

11 Claims, No Drawings

WATER-SOLUBLE TRIPHENDIOXAZINE COMPOUNDS AND THEIR USE AS DYESTUFFS

DESCRIPTION

The invention relates to the technical field of fiber-reactive dyestuffs.

Dyestuffs, but not triphendioxazine dyestuffs, which contain a {bis-[β-(β'-chloroethylsulfonyl)-ethyl]-amino}-or {bis[β-(β'-sulfatoethylsulfonyl)-ethyl]-amino}-chloro-s-triazinyl or -fluoro-s-triazinyl radical as a fiber-reactive group are known from British Patent Specification 1,576,237 and European Patent Application Publications Nos. 0 070 807 and 0 074 928. Where triphendioxazine dyestuffs are described in these publications, they contain a [β-(β'-(sulfatoethylsulfonyl)-ethyl-amino]-, [β-(β'-chloroethylsulfonyl)-ethylamino]-or [γ-(β'-chloroethylsulfonyl)-propylamino]-chloro-s-triazinyl or -fluoro-s-triazinyl radical or the 2-{bis-[β-(β'-sulfatoethylsulfonyl)-ethyl]-amino}-4-fluoro-1,3,5-triazin-6-yl-amino radical as the fiber-reactive grouping. However, triphendioxazine dyestuffs of this type have certain disadvantages in their use, partly because of their poor water-solubility or too high a fiber substantivity.

With the present invention, novel triphendioxazine compounds having good fiber-reactive dyestuff properties have now been found, which correspond to the formula (1)

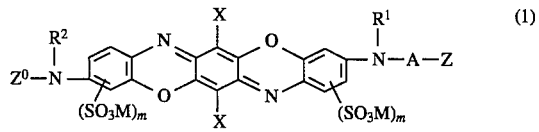

In this formula:

M is hydrogen or an alkali metal, such as sodium, potassium or lithium;

m is the number 1 or 2, preferably 1, where a group —$SO_3M$ is preferably bonded in the ortho-position relative to the oxy group;

X is hydrogen, halogen, such as chlorine or bromine, optionally substituted alkyl having 1 to 4 carbon atoms, such as methyl or ethyl, optionally substituted aryl, such as phenyl or naphthoxy, optionally substituted aryloxy, such as phenoxy or naphthoxy, cyano, alkoxycarbonyl having 2 to 5 carbon atoms, such as methoxycarbonyl or ethoxycarbonyl, optionally substituted aryloxycarbonyl, such as phenoxycarbonyl or naphthoxycarbonyl, aminocarbonyl, N-alkyl-aminocarbonyl with an alkyl radical having 1 to 4 carbon atoms, N,N-dialkyl-aminocarbonyl with alkyl radicals having in each case 1 to 4 carbon atoms, optionally substituted alkylcarbonyl having 2 to 5 carbon atoms, such as acetyl or propionyl, or optionally substituted arylcarbonyl, and is preferably chlorine, methyl, ethyl, methoxy or phenyl and particularly preferably chlorine;

$R^1$ is hydrogen or optionally substituted alkyl having 1 to 6 carbon atoms, preferably 1 to 4 carbon atoms, or is optionally substituted aryl, and is preferably hydrogen;

$R^2$ has one of the meanings given for $R^1$;

Z is a radical of the formula (2)

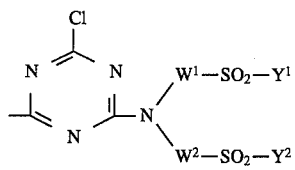

in which $Y^1$ is vinyl or is ethyl which contains a substituent in the β-position which can be eliminated by means of alkali to form the vinyl group, or is β-hydroxyethyl, $Y^2$ has one of the meanings of $Y^1$, and preferably has the same meaning as $Y^1$, with the proviso that $Y^1$ and $Y^2$ are not simultaneously β-hydroxyethyl, $W^1$ is alkylene having 2 to 6 carbon atoms, preferably 2 or 3 carbon atoms, such as, in particular, 1,2-ethylene or 1,3-propylene, and $W^2$ has one of the meanings given for $W^1$, and preferably has the same meaning as $W^1$;

A is a covalent bond or a group of the formula (3a)

in which $R^3$ has one of the meanings given for $R^1$ and $B^1$ is alkylene having 2 to 6 carbon atoms, preferably 2 or 3 carbon atoms, such as 1,2-ethylene or 1,3-propylene, or is alkylene having 3 to 10 carbon atoms, preferably 4 to 8 carbon atoms, which is interrupted by 1 or 2 hetero groups, such as groups of the formulae —O—, —NH—, —S—, —$SO_2$—, —CO—, —NH—CO—, —NH—$SO_2$—, —$SO_2$—NH—, —CO—NH—, —NH—CO—NH—, —NH—CO—O—, —CO—O—, —O—OC—NH—, —O—OC— or —N(R)—, where R is alkyl having 1 to 4 carbon atoms, such as methyl or ethyl, or is cycloalkylene having 5 to 8 carbon atoms, such as cyclohexylene, or is a radical of the formula phen, naphth, alk-phen, phen-alk, naphth-alk, alk-naphth, phen-alk-phen, alk-phen-alk, phen-D-phen, alk-D-phen, phen-D-alk, cy-alk, alk-cy, cy-alk-cy or alk-cy-alk, in which phen is phenylene, which can be substituted by 1 or 2 substituents from the group consisting of methyl, ethyl, methoxy, sulfo and carboxy, naphth is naphthylene, which can be substituted by 1 or 2 sulfo groups, alk is alkylene having 1 to 6 carbon atoms, preferably 2 to 4 carbon atoms, which can be substituted by 1 or 2 substituents from the group consisting of hydroxy, acetyloxy, sulfo, carboxy and sulfato and/or can be interrupted by one of the abovementioned hetero groups, cy is cycloalkylene having 5 to 8 carbon atoms, such as cyclohexylene, and D is one of the abovementioned hetero groups, or the group —$N(R^1)$—$B^1$—$N(R^3)$— in total is a bivalent saturated heterocyclic radical, such as the 1,4-piperazinylene radical; and $Z^0$ is hydrogen, or is a group of the formula (4)

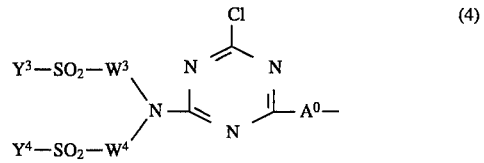

in which $Y^3$ and $Y^4$ have one of the meanings given above for $Y^1$, and $Y^3$ and $Y^4$ preferably have the same meaning as one another, $W^3$ and $W^4$ have one of the meanings given above for $W^1$, and $W^3$ and $W^4$ preferably have the same meaning as one another, and $A^0$ is a covalent bond or a radical of the formula (3b)

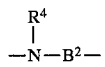 (3b)

in which $R^4$ has one of the meanings given above for $R^1$ and $B^2$ has one of the meanings given above for $B^1$, or the group —N($R^4$)—$B^2$—N($R^2$)— is a bivalent saturated heterocyclic radical, such as the 1,4-piperazinylene radical.

In the abovementioned formulae and also in the following formulae, the individual formula members, both of different and the same meaning, can have meanings which are identical to one another or different from one another in the context of their definition within a general formula.

Substituents in the β-position in the abovementioned ethyl groups Y are, for example, sulfato, thiosulfato, phosphato, alkanoyloxy having 2 to 5 carbon atoms, such as acetyloxy, benzoyloxy, sulfobenzoyloxy, p-toluene-sulfonyloxy or halogen, such as chlorine or bromine, and of these preferably sulfato, and in particular chlorine. The groups Y furthermore are preferably vinyl.

The "sulfo", "carboxy", "phosphato", "thiosulfato" and "sulfato" groups include both the acid form thereof and the salt form thereof. Accordingly, sulfo groups are groups corresponding to the formula —$SO_3M$, carboxy groups are groups corresponding to the formula —COOM, phosphato groups are groups corresponding to the formula —$OPO_3M_2$, thiosulfato groups are groups corresponding to the formula —S—$SO_3M$ and sulfato groups are groups corresponding to the formula —$OSO_3M$, in which M has the abovementioned meaning.

Substituents in the substituted alkyl groups X, $R^1$, $R^2$, $R^3$ and $R^4$ are, for example, methoxy, ethoxy, hydroxy, alkanoyloxy having 2 to 5 carbon atoms, such as acetyloxy, sulfo, carboxy, sulfato and chlorine. Aryl radials are, for example, phenyl radicals or naphthyl radicals. Substituted aryl radicals are, for example, those which are substituted by 1, 2 or 3 substituents from the group consisting of sulfo, carboxy, methoxy, ethoxy, methyl, ethyl, chlorine and bromine. Substituted naphthyl radicals are, in particular, those which are substituted by 1 to 3 sulfo groups and/or a carboxy group.

Radicals $W^1$, $W^2$, $W^3$ and $W^4$ are, for example, 1,2-ethylene, 1,3-propylene, 1,4-butylene, 1,5-pentylene, 1,6-hexylene, 2-methyl-1,3-propylene and radicals of the formulae —$CH_2$—CH($CH_3$), —CH($CH_3$)—$CH_2$— and —$(CH_2)_2$—O—$(CH_2)_2$—.

Radicals $B^1$ are, for example, 1,2-ethylene, 1,3-propylene, 1,4-butylene, 1,5-pentylene, 1,6-hexylene, 2-methyl-1,3-propylene, 1,4-cyclohexylene, 1,4-phenylene, 1,3-phenylene, 2,5-disulfo-1,4-phenylene, 2,5-disulfo-1,3-phenylene, 3-sulfo-1,4-phenylene, 2-sulfo-1,4-phenylene, 5-sulfo-1,3-phenylene and radicals of the formulae —$CH_2$—CH($CH_3$)—, —CH($CH_3$)—$(CH_2)_2$—, —$(CH_2)_2$—NH—$(CH_2)_2$—, —$(CH_2)_3$—NH—$(CH_2)_3$—, —$(CH_2)_2$—NH—$(CH_2)_3$—, —$(CH_2)_3$—NH—$(CH_2)_2$—, —$(CH_2)_2$—O—$(CH_2)_2$—, —$(CH_2)_2$—O—$(CH_2)_3$—, —$(CH_2)_3$—O—$(CH_2)_3$—, —$(CH_2)_3$—O—$(CH_2)_2$—$(CH_2)_2$NH—CO—NH—$(CH_2)_2$—, —$(CH_2)_2$—NH—$SO_2$—$(CH_2)_2$—, —$(CH_2)_2$—CO—NH—$(CH_2)_2$—, —$(CH_2)_2$—$SO_2$NH—$(CH_2)_2$—, —$(CH_2)_2$—COO—$(CH_2)_2$—, —$(CH_2)_2$—OOC—$(CH_2)_2$—, —$(CH_2)_2$—NH—COO—$(CH_{22}$— or —$(CH_2)_2$—NH—CO—NH—$(CH_2)_2$— or of the formula

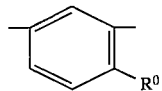

in which $R^0$ is methoxy or methyl. Preferably, $B^1$ is ethylene or propylene, or phenylene which is substituted by 1 or 2 sulfo groups.

Radicals $B^2$ are for example, 1,2-ethylene, 1,3-propylene, 1,4-butylene, 1,5-pentylene, 1,6-hexylene, 2-methyl-1,3-propylene, 1,4-cyclohexylene, 1,4-phenylene, 1,3-phenylene, 2,5-disulfo-1,4-phenylene, 2,5-disulfo-1,3-phenylene, 3-sulfo-1,4-phenylene, 2-sulfo-1,4-phenylene, 5-sulfo-1,3-phenylene, and radicals of the formulae —$CH_2$—CH($CH_3$)—, —CH($CH_3$)—$CH_2$—, —$(CH_2)_2$—NH—$(CH_2)_2$—, —$(CH_2)_3$—NH—$(CH_2)_3$—, —$(CH_2)_2$—NH—$(CH_2)_3$—, —$(CH_2)_3$—NH—$(CH_2)_2$—, —$(CH_2)_2$—O—$(CH_2)_2$—, —$(CH_2)_2$—O—$(CH_2)_3$—, —$(CH_2)_3$—O—$(CH_2)_3$—, —$(CH_2)_3$—O—$(CH_2)_2$—$(CH_2)_2$NH—CO—$(CH_2)_2$—, —$(CH_2)_2$NH—$SO_2$—$(CH_2)_2$—, —$(CH_2)_2$—CO—NH—$(CH_2)_2$—, —$(CH_2)_2$—$SO_2$—NH—$(CH_2)_2$—, —$(CH_2)_2$—COO—$(CH_2)_2$—, —$(CH_2)_2$OCC—$(CH_2)_2$—, —$(CH_2)_2$—NH—COO—$(CH_2)_2$— or —$(CH_2)_2$—NH—CO—NH—$(CH_2)_2$— or of the formula

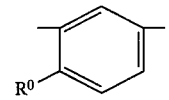

where $R^0$ is methoxy or methyl. Preferably, $B^2$ is ethylene or propylene, or phenylene which is substituted by 1 or 2 sulfo groups.

Radicals X are, for example, chlorine, bromine, fluorine, iodine, methyl, ethyl, n-propyl, isopropyl, methoxy, ethoxy, phenyl, 4-methyl-phenyl, 2-methyl-phenyl, 2-chloro-phenyl, 4-chloro-phenyl, 4-sulfo-phenyl, 3-sulfo-phenyl, phenoxy, 4-methyl-phenoxy, 4-sulfo-phenoxy, 3-sulfo-phenoxy, cyclohexyl, cyclopentyl, benzyl, cyano, ethoxycarbonyl, methoxycarbonyl, phenoxy-carbonyl, acetyl, propionyl, phenylcarbonyl, amino, methylamino, dimethylamino, ethylamino and diethylamino.

Particularly preferred triphendioxazine compounds of the formula (1) are those in which A is a covalent bond, X is chlorine and $Z^0$ is hydrogen, and $R^1$ and $R^2$ are each hydrogen.

Preferred triphendioxazine compounds of the formula (1) are furthermore those in which A is a radical of the formula (3a), X is chlorine and $Z^0$ is hydrogen or a radical of the formula (4), wherein $A^0$ is a radical of the formula (3b). Of these compounds, those in which $R^1$, $R^2$, $R^3$ and $R^4$ are each hydrogen and $B^1$ or $B^2$ or both have one of the preferred meanings are in turn preferred.

Triphendioxazine compounds of the formula (1) which are furthermore to be singled out are those in which the formula radical (5)

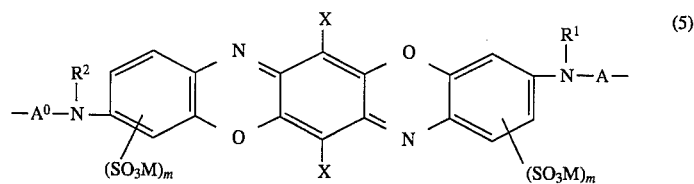
is a radical of the formula (5A), (5B), (5C), (5D), (5E), (5F) or (5G)
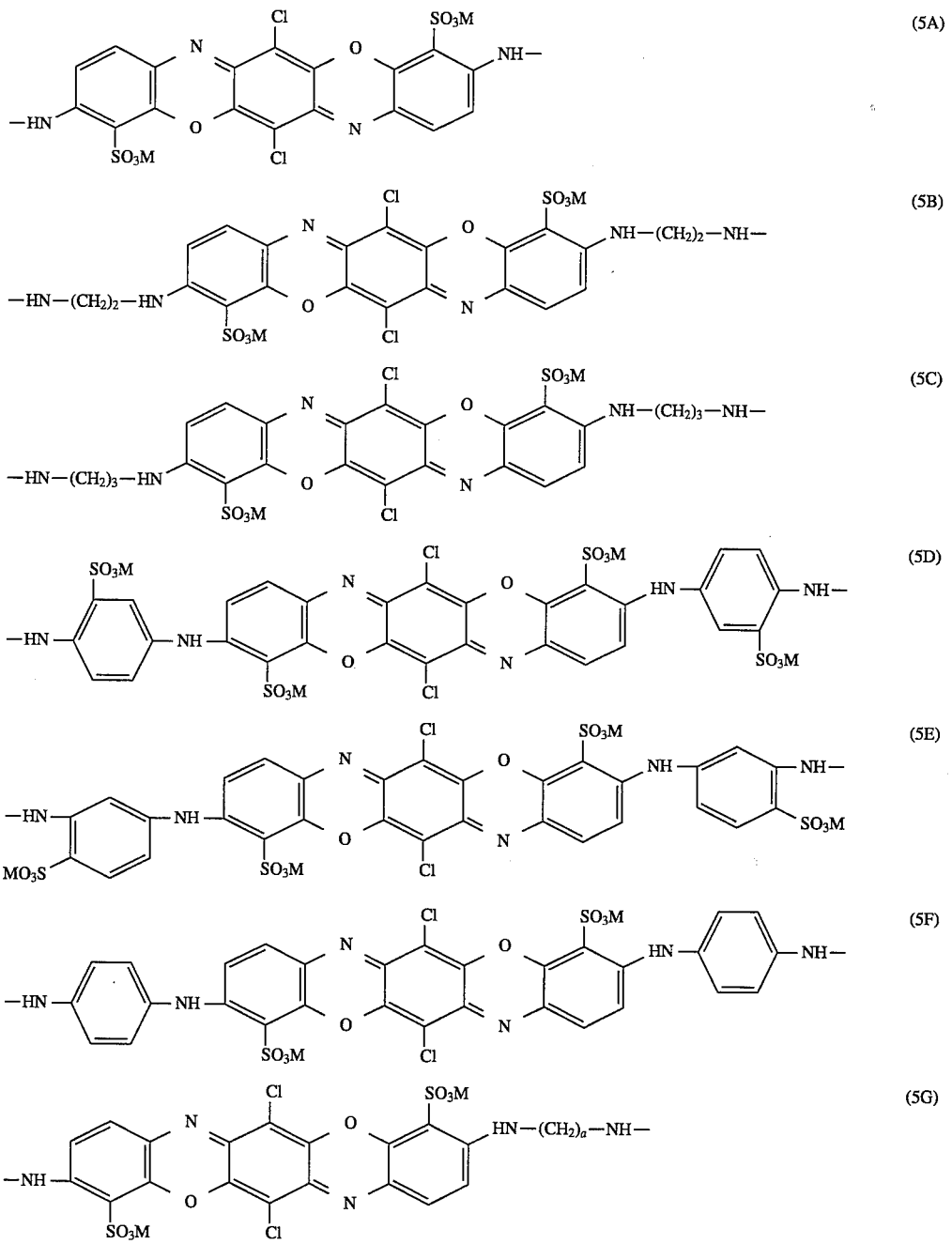
in which M has the abovementioned meaning and a is the number 2 or 3.

Radicals of the formula (6a) and (6b)

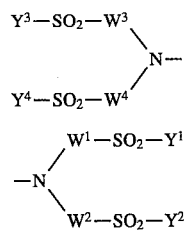

in the triphendioxazine compounds of the formula (1) are, for example, bis-N,N-[β-(β'-chloroethylsulfonyl)-ethyl]-amino, bis-N,N-[β-vinylsulfonyl-ethyl]-amino, bis-N,N-[β-(β'-sulfatoethylsulfonyl)-ethyl]-amino, bis-N,N-[γ-(β'-chloroethylsulfonyl)-propyl]-amino, bis-N,N-[γ-vinylsulfonyl-propyl]-amino, bis-N,N-[γ-(β'-sulfatoethyl-sulfonyl)-propyl]-amino, bis-N,N-[β-(β'-chloroethylsulfonyl)-isopropyl]-amino, bis-N,N-[β-vinylsulfonylisopropyl]-amino, bis-N,N-[β-(β'-sulfatoethylsulfonyl)-isopropyl]-amino, bis-N,N-[δ-(β'-chloroethylsulfonyl)-butyl]-amino, bis-N,N-[γ-(β'-chloroethylsulfonyl)-isobutyl]-amino and bis-N,N-[β-(β'-chloroethylsulfonyl)-isobutyl]-amino.

Triphendioxazine compounds according to the invention which are to be singled out in particular are those which correspond to the formulae (1A), (1B), (1C), (1D) and (1E)

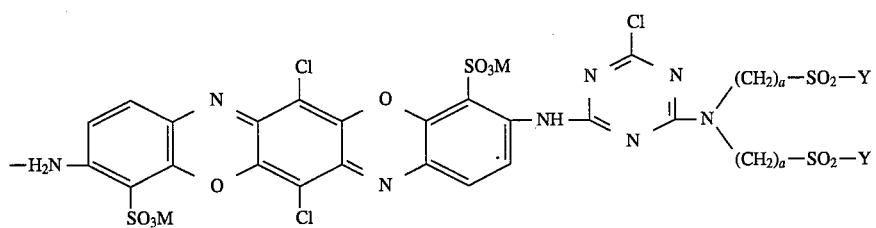
(1A)

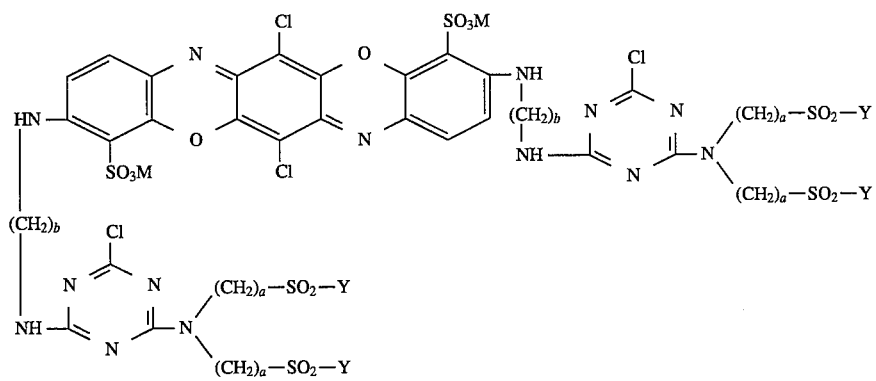
(1B)

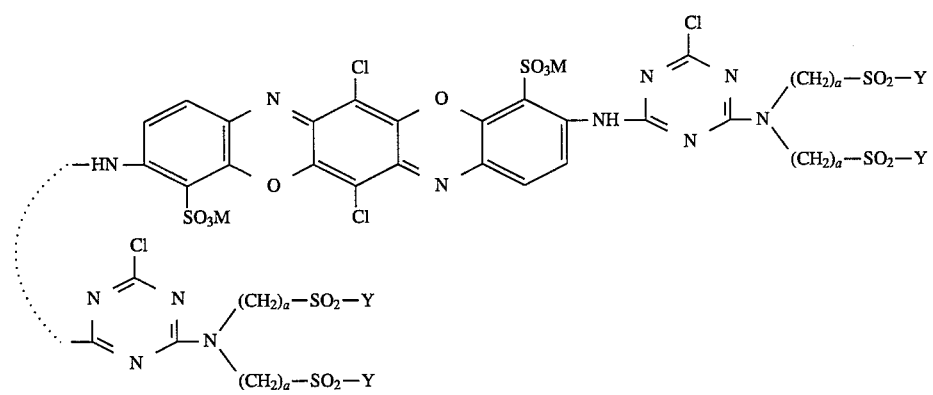
(1C)

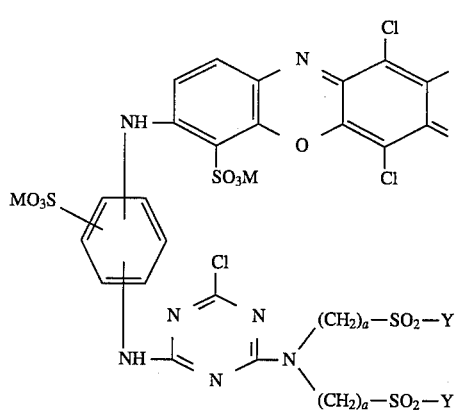
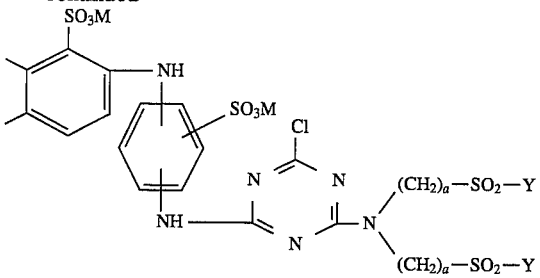

(1D)

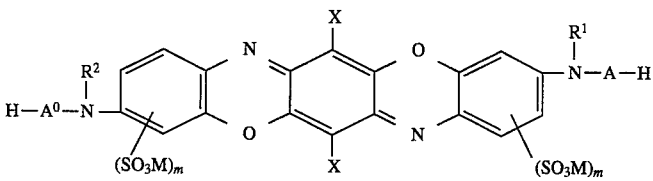

(1E)

in which M has the abovementioned meaning, a is the number 2 or 3, b is the number 2 or 3 and Y is β-chloroethyl or vinyl, and where the two or four groups Y in each case can be the same as one another or different from one another.

The present invention furthermore relates to a process for the preparation of the triphendioxazine compounds of the formula (1) according to the invention, which comprises reacting cyanuric chloride (2,4,6-trichloro-1,3,5-triazine) in any desired sequence with a triphendioxazine compound containing amino groups, of the formula (7)

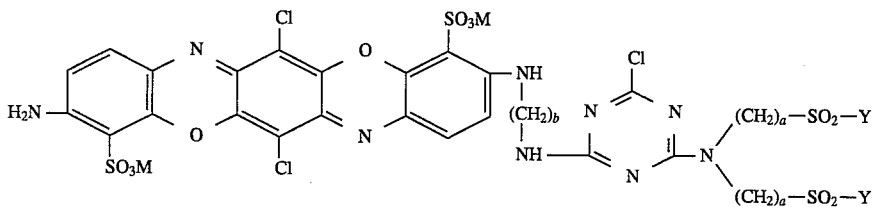

(7)

where $A^0$, A, X, M, m, $R^1$ and $R^2$ have the abovementioned meaning, and with an amine of the formula (8a) and/or (8b)

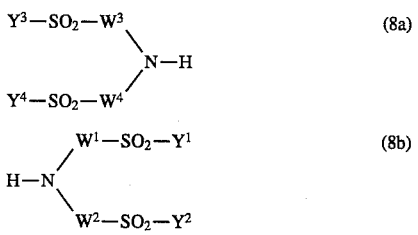

(8a)

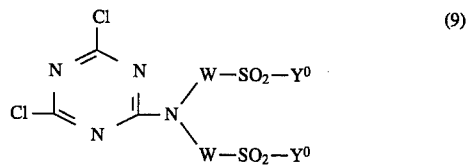

(8b)

wherein $W^1$, $W_2W^3$, $W^4$, $Y^1$, $Y^2$, $Y^3$ and $Y^4$ have the abovementioned meaning, or with a salt of the amine with an inorganic or organic acid customary in the art, such as hydrochloric acid, sulfuric acid, phosphoric acid or acetic acid, in an equivalent amount at a temperature of between 0° C. and 100° C. and at a pH of between 2 and 10, preferably between 4 and 9.

Triphendioxazine compounds of the formula (1) according to the invention in which A is a covalent bond and $Z^0$ is a group of the formula (4), where $A^0$ is a covalent bond, are preferably prepared according to the invention by reacting a triphendioxazine compound of the formula (7) in which A and $A^0$ are both a covalent bond with a compound of the formula (9)

$$\begin{array}{c} \text{Cl} \\ | \\ \text{N} \overset{\diagup}{\phantom{x}} \text{N} \quad W-SO_2-Y^0 \\ \text{Cl}-\overset{|}{\underset{N}{\diagdown}}\overset{}{\phantom{x}}\text{N} \\ \phantom{xxxxxxxxx} W-SO_2-Y^0 \end{array}$$

(9)

in which each W, which radicals are identical to one another or different from one another, and each $Y^0$, which radicals are identical to one another or different from one another, has one of the meanings of $W^1$, $W^2$, $W^3$ and $W^4$ or, respectively, $Y^1$, $Y^2$, $Y^3$ and $Y^4$, employing 4 to 6 times the molar amount of the compound (9), at a temperature of between 60° and 95° C., preferably between 70° and 90° C., and at a pH of 4 to 5.

Triphendioxazine dyestuffs of the formula (1) according to the invention in which $Z^0$ is hydrogen and A is a covalent bond are preferably prepared according to the invention by reacting a compound of the formula (7), where A and $A^0$ are a covalent bond, with a compound of the formula (9) of the abovementioned meaning at a temperature of between 60° and 95° C., preferably between 70° and 90° C., and at a pH of between 3 and 6, preferably between 4 and 5, using 2 to 3 times the molar amount of compound (9).

Triphendioxazine compounds of the formula (1) according to the invention in which A is a radical of the formula (3a) and $Z^0$ is a radical of the formula (4), where $A^0$ is a radical of the formula (3b), are preferably prepared according to the invention by first reacting a triphendioxazine compound of the formula (7), in which A and $A^0$ have the meanings just given, with cyanuric chloride at a temperature of between −5° C. and 20° C., preferably between 0° and 10° C., and at a pH of between 8 and 10, preferably between 8.5 and 9, and re acting the bis-(dichloro-triazinylamino)-triphendioxazine compound thus obtained with an amino compound of the formula (8a) and/or (8b) at a temperature of between 60 ° and 90° C., preferably between 70° and 80° C., and at a pH of between 5 and 8, preferably between 6 and 7, or by reacting a triphendioxazine compound of the formula (7), where A and $A^0$ have the meanings just given, with a compound of the formula (9) at a temperature of between 60° and 95° C., preferably between 70° and 90° C., and a pH of between 3 and 6, preferably between 4 and 5.

The reactions of the triphendioxazine compounds of the formula (7) with cyanuric chloride or with a compound of the formula (9) or the reaction of the bis-(dichloro-triazinylamino)-triphendioxazine compound with an amine (8a) and/or (8b) can be carried out in either an aqueous or aqueous-organic medium in suspension or solution. If the reactions are carried out in an aqueous-organic medium, the organic medium, which is, for example, acetone, dimethylformamide, dimethylacetamide, dimethyl sulfoxide or N-methyl-pyrrolidone, can be present in a mixing ration of up to 40% by volume. Hydrochloric acid liberated during the condensation reaction is advantageously neutralized continuously be addition of aqueous alkali metal or alkaline earth metal hydroxides, carbonates or bicarbonates.

The starting compounds are known, for example, from the abovementioned publications and form U.S. Pat. Nos. 3,883, 523 and 4,568,742 and European Patent 0 101 665, or can be prepared analogously to the instructions given therein.

The compounds of the formula (1) prepared according to the invention are separated off from the synthesis batches by generally known methods, either by precipitation from the reaction medium by means of electrolytes, such as, for example, sodium chloride or potassium chloride, or by evaporation of the reaction solution, for example by spray drying, it being possible for a buffer substance to be added to this reaction solution.

The compounds of the formula (1)—called "dyestuffs (1)" below—have fiber-reactive dyestuff properties and can be used for dyeing (including printing)materials containing hydroxy, amino and/or carboxamide groups, in particular fiber materials. The present invention therefore also relates to the use of the dyestuffs (1) for dyeing such materials, and to processes for dyeing such materials in which the dyestuff (1) is introduced in dissolved form onto the material or into the material and is fixed by means of heat or under the action of an alkaline agent, or with the aid of both measures.

Materials containing hydroxy groups are those of natural or synthetic origin, such as, for example, cellulose fiber materials, such as naturally occurring cellulose fibers, or regenerated products thereof and polyvinyl alcohols. Cellulose fiber materials are preferably cotton, but also other plant fibers, such as linen, hemp, jute and ramie fibers; regenerated cellulose fibers are, for example, viscose staple fibers and filament viscose.

Materials containing carboxamide groups are, for example, synthetic and naturally occurring polyamides and polyurethanes, in particular in the form of fibers, such as, for example, wool and other animal hair, silk, leather, polyamides 6,6, polyamide 6, polyamide 11 and polyamide 4.

Materials containing amino groups are likewise, for example, polyamides, such as synthetic polyamides from the series consisting of polyamide 6,6, polyamide 4, polyamide 11 and polyamide 6, or naturally occurring protein fibers, such as wool, silk, leather and animal hair, in particular cellulose fibers modified by amino groups, such as cotton modified by amino groups.

The dyestuffs (1) can be applied to the fiber material and fixed on the fiber in various ways, in particular in the form of aqueous dyestuff solutions and printing pastes. Such processes are known in numerous instances from the literature (cf., for example, European Patent Application Publication No. 0 181 585). They are suitable both for the generally known exhaustion process in wide temperature ranges, such as form 40° to 90° C., preferably 60° to 80° C., and for dyeing by the pad-dyeing process, in which he goods are impregnated with the aqueous dyestuff solution and the dyestuff is fixed, after an alkali treatment or in the presence of alkali, if appropriate under the action of heat, for example by steaming. The dyestuffs (1) are preferably employed in the exhaustion process. High-quality dyeings are also obtained in this process if the dyebath comprises only a small amount of one or more electrolyte salts, such as sodium chloride, potassium chloride and sodium sulfate, for example 20 to 40 g/l of dye liquor, in contrast to the amounts of 50 to 80 g/l generally used in the art. They are also preferably used for dyeing in the pad-cold batch process. After fixing, the dyeings or prints are rinsed thoroughly with cold and hot water, if appropriate with the addition of a dispersing agent which promotes diffusion of the non-fixed portions.

The dyestuffs (1) are distinguished by a high reactivity, good fixing capacity and a good build-up capacity. The dyeings obtainable have a high levelness. The degrees of fixing are high and non-fixed portions can easily be washed out. The dyestuffs (1) are also suitable for printing, above all on cotton, but also for printing nitrogen-containing fibers, for example wool or silk, or blended fabrics which contain wool or silk.

The dyeings and prints produced with the dyestuffs (1), in particular on cellulose fiber material, have a high brilliance, a good depth of color and a high fiber-dyestuff bond stability both in the acid and in the alkaline range, and furthermore a good lightfastness and very good wet-fastness properties, such as fastnesses to washing, water, sea water, cross-dyeing and perspiration, as well as a good fastness to pleating, fastness to ironing and fastness to rubbing.

The following Examples serve to illustrate the invention. The parts are parts by weight and the percentage data are percentages by weight, unless noted otherwise. Parts by weight are in the same ratio to parts by volume as the kilogram to the liter.

The compounds described by the formulae in the Examples are shown in the form of the free acid; in general, they are prepared and isolated in the form of their alkali metal salts, such as lithium, sodium or potassium salts, and are used for dyeing in the form of their salts. The starting compounds and components mentioned in the form of the free acid in the following Examples, in particular the Tabular Examples, can likewise be employed in the synthesis as such or in the form of their salts, preferably alkali metal salts.

The absorption maxima ($\lambda_{max}$) in the visible range stated for the dyestuffs according to the invention were determined with the aid of their alkali metal salts in aqueous solution. In the Tabular Examples, the $\lambda_{max}$ values are given in parentheses where the color shade is stated; the wavelength data are in nm.

EXAMPLE 1

5.89 parts of the triphendioxazine compound of the formula (10)

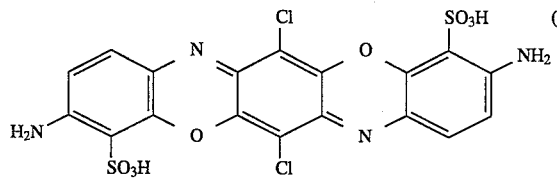
(10)

(which can be prepared in accordance with the instructions of European Patent Application Publication No. 0 170 838) are stirred into 1500 parts of water, dissolved by means of 5 parts of lithium hydroxide and reacted with 47.4 parts of the compound 6-{bis-N,N-[β-(β'-chloroethylsulfonyl)-ethyl]-amino}-2,4-dichloro-1,3,5-triazine at a temperature of about 80° C. for about five hours, while stirring and maintaining a pH of 4.5 by means of an aqueous lithium carbonate solution. The resulting triphendioxazine compound according to the invention of the formula (written in the form of the free acid).

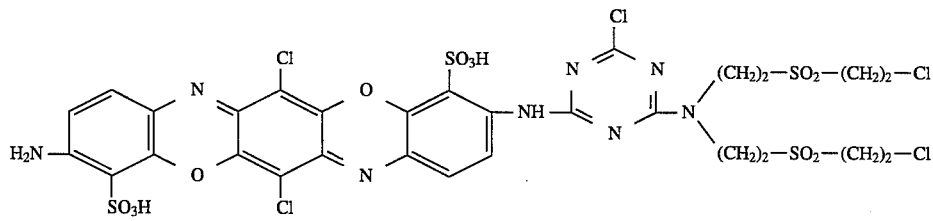

($\lambda_{max}$ = 570 nm)

is isolated as the sodium slat from the synthesis solution in the customary manner by salting out with sodium chloride. It shows very good fiber-reactive dyestuff properties and dyes the fiber materials mentioned in the description, such as, in particular, cellulose fiber materials, in brilliant reddish blue shades with a high degree of fixing by the dyeing and printing processes customary in the art for fiber-reactive dyestuffs. Non-fixed residues of the dyestuff can easily be washed out of the resulting dyeing. The dyeing has a very high levelness.

EXAMPLE 2

58.9 parts of the lithium salt of the triphendioxazine compound of the formula (10) are stirred into 1500 parts of water and reacted with 120 parts of the compound 6-{bis-N,N-[β-(β'-chloroethylsulfonyl)-ethyl]-amino}-2,4-dichloro- 1,3,5-triazine at a pH of between 4.5 and 6 and at a temperature of 75° to 85° C. for about six hours, while stirring. The triphendioxazine compound according to the invention of the formula (written in the form of the free acid)

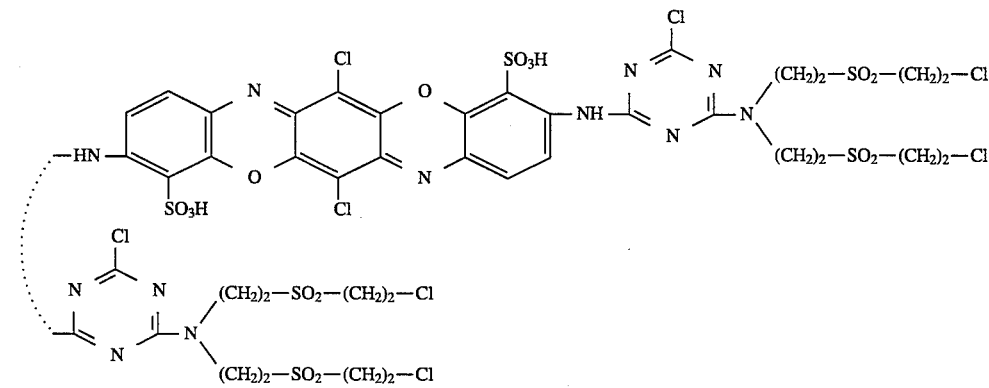

($\lambda_{max}$ = 568 nm)

is obtained as a mixture with the partly vinylized form therof. It is isolated as the alkali metal salt from the synthesis solution in the customary manner, for example by salting out by means of sodium chloride. The compound according to the invention has very good fiber-reactive dyestuff properties and dyes the materials mentioned in the description, such as, in particular, cellulose fiber materials, in brilliant reddish blue shades with a high degree of fixing by the application and fixing processes customary in the art for fiber-reactive dyestuffs. The dyeings have a high levelness, and non-fixed residues of the dyestuff on the dyeing can easily be washed out.

EXAMPLE 3

To prepare the analogous vinylsulfonyl compound of the triphendioxazine compound according to the invention obtained of Example 1, concentrated aqueous sodium hydroxide solutions added up to a pH of 11.5 to 12 to the aqueous synthesis solution of the compound according to the invention of Example 1 at a temperature of 20° to 25° C., while stirring thoroughly. The mixture is subsequently stirred for about a further 30 minutes, while maintaining this pH range and a temperature of 20° to 25° C., a pH of 6 is then established and the dyestuff according to the invention (written in the form of the free acid)

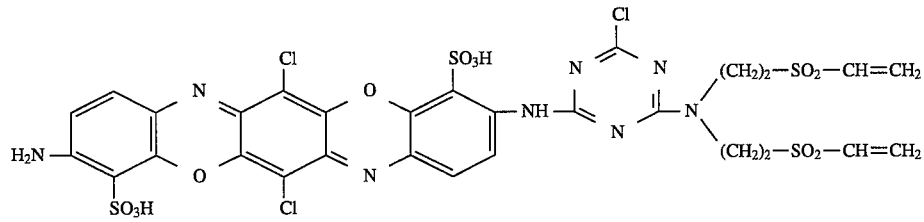

($\lambda_{max}$ = 569 nm)

is isolated as the sodium salt from the synthesis solution in the customary manner, for example by salting out with sodium chloride. The vinylsulfonyl compound according to the invention dyes, for example, cellulose fiber materials in brilliant reddish blue shades in a good depth of color and with a high degree of fixing in the same manner.

EXAMPLE 4

61.7 parts of the triphendioxazine compound of the formula

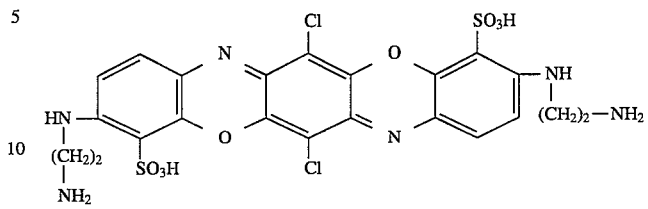

(which can be prepared in accordance with the instructions of European Patent Application Publication No. 0 486 429) are dissolved in 1000 parts of water at a pH of 11 to 12 by means of lithium hydroxide, and a solution, brought to a pH of 6.5 to 7, of 98 parts of the compound 6-{bis-N,N-[β-(β'-chloroethylsulfonyl)-ethyl]-amino}-2,4-dichloro-1,3,5-triazine in 500 parts of water is slowly added to this solution, while stirring thoroughly, the pH of the reaction mixture being kept at a pH of between 6.5 and 7 first with dilute aqueous acetic acid and later with an aqueous lithium carbonate solution. The reaction temperature of the batch is then increased to 70° to 80° C. and stirring of the batch is continued within this temperature range and at a pH of between 6.5 and 7 until the reaction has ended.

The triphendioxazine compound according to the invention which has been synthesized and which, written in the form of the free acid, corresponds to the formula

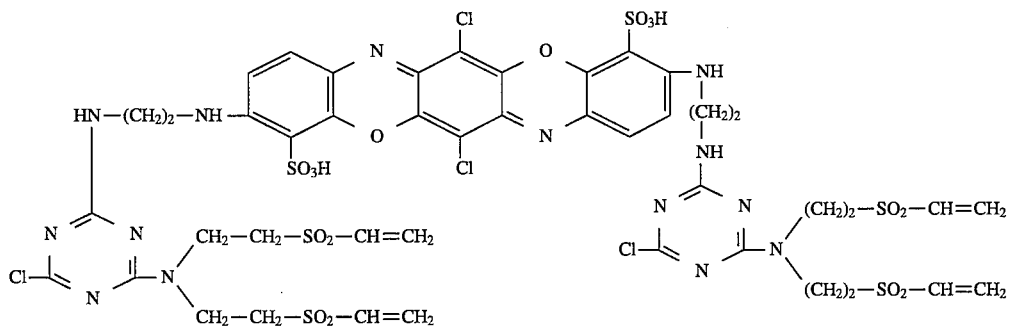

($\lambda_{max}$ = 615 nm)

is isolated as the alkali metal salt (sodium salt) in the customary manner, for example by salting out with sodium chloride. It has very good dyestuff properties and gives, for example, deep dyeings and prints in brilliant greenish blue shades on cellulose fiber materials by the application and fixing processes customary in the art for fiber-reactive dyestuffs.

EXAMPLE 5

61parts of the triphendioxazine compound of the formula

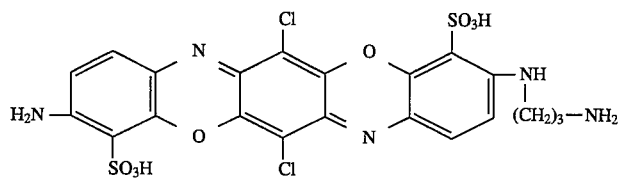

known from European Patent Application Publication No. 0 485 329 are dissolved as the lithium salt in 1000 parts of water at a pH of 10. 98 parts of the compound 6-{bis-N, N-[β-(β'-chloroethylsulfonyl)-ethyl]-amino}-2,4-dichloro-1,3,5-triazine are slowly added to the solution at 20° to 25° C. The reaction batch is stirred at a pH of between 8 and 9 and at a temperature of between 70° and 80° C. until the reaction has ended, the batch is then cooled to room temperature, the pH is brought to 6 and the compound according to the invention of the formula

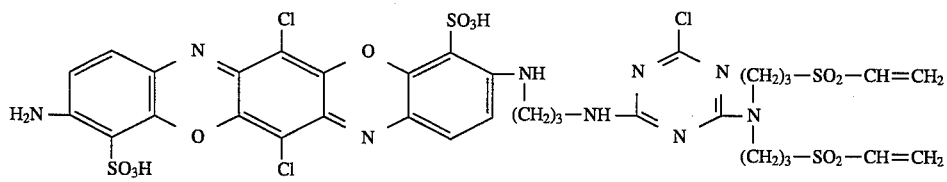

($\lambda_{max}$ = 599 nm)

is isolated as the sodium salt by salting out with sodium chloride.

The triphendioxazine compound according to the invention shows very good fiber-reactive dyestuff properties and dyes the materials mentioned in the description, such as, in particular, cotton, in brilliant blue shades with a good depth of color and good fastness properties.

EXAMPLES 6 TO 27

Further triphendioxazine compounds according to the invention corresponding to a formula (A)

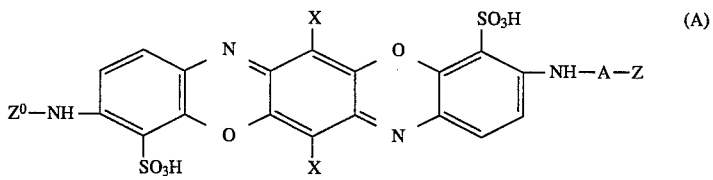

are described with the aid of their components in the following Tabular Examples. They can be prepared by the procedure according to the invention, such as, for example, analogously to one of the above Examples, using the starting compounds which can be seen form the components of the formula (A). They have very good fiber-reactive dyestuff properties and give deep, fast dyeings and prints in the color shade shown in the particular Tabular Example on the materials mentioned in the description, such as, in particular, cellulose fiber materials, by the customary processes for their use.

| | Triphendioxazine compound (A) | | | | |
|---|---|---|---|---|---|
| Example | Radical $Z^0$ | Radical X | Radical A | Radical Z | Color shade |
| 6 | hydrogen | chlorine | covalent bond | 4-{bis-N,N-[γ'-(β'-chloroethyl-sulfonyl)-propyl]-amino}-2-chloro-1,3,5-triazin-6-yl | reddish blue (565) |
| 7 | hydrogen | chlorine | covalent bond | 4-{bis-N,N-(γ-vinyl-sulfonyl-propyl)-amino}-2-chloro-1,3,5-triazin-6-yl | reddish blue (566) |
| 8 | 4-{bis-N,N-(γ-vinyl-sulfonyl-propyl)-amino}-2-chloro-1,3,5-triazin-6-yl | chlorine | covalent bond | 4-{bis-N,N-(γ-vinyl-sulfonyl-propyl)-amino}-2-chloro-1,3,5-triazin-6-yl | reddish blue (561) |
| 9 | β-{4-bis-N,N-[γ'-(β''-chloroethyl-sulfonyl)-propyl-amino]-2-chloro-1,3,5-triazin-6-ylamino}-ethyl | chlorine | —CH$_2$—CH$_2$—NH— | 4-{bis-N,N-[γ'-(β''-chloroethyl-sulfonyl)-propyl]-amino}-2-chloro-1,3,5-triazin-6-yl | greenish blue (616) |
| 10 | β-{4-bis-N,N-[β'-(β''-chloroethyl-sulfonyl)-β'-methyl-ethylamino]-2-chloro-1,3,5-triazin-6-ylamino}-isopropyl | chlorine | —CH(CH$_3$)—CH$_2$—NH— | 4-{bis-N,N-[γ-(β'-chloroethyl-sulfonyl)-propyl]-amino}-2-chloro-1,3,5-triazin-6-yl | greenish blue (614) |
| 11 | γ-{4-bis-N,N-[β'-(β''-chloroethyl-sulfonyl)-ethyl-amino]-2-chloro-1,3,5-triazin-6-yl-amino}-propyl | chlorine | —(CH$_2$)$_3$—NH— | 4-{bis-N,N-[β-(β'-chloroethyl-sulfonyl)-ethyl]-amino}-2-chloro-1,3,5-triazin-6-yl | greenish blue (615) |
| 12 | 2-sulfo-4-{4'-bis-N,N-[β'-(β''-chloro-ethylsulfonyl)-ethyl-amino]-2'-chloro-1',3',5'-triazin-6'-ylamino}-phen-1-yl | chlorine | 3-SO$_3$H, 4-NH— phenyl | 4-{bis-N,N-[β-(β'-chloroethyl-sulfonyl)-ethyl]-amino}-2-chloro-1,3,5-triazin-6-yl | greenish blue (639) |
| 13 | 3-sulfo-4-{4'-bis-N,N-[β'-(β''-chloro-ethylsulfonyl)-ethyl-amino]-2'-chloro-1',3',5'-triazin-6'-ylamino}-phen-1-yl | chlorine | 2-SO$_3$H, 1-NH— phenyl | 4-{bis-N,N-[β-(β'-chloroethyl-sulfonyl)-ethyl]-amino}-2-chloro-1,3,5-triazin-6-yl | greenish blue (640) |
| 14 | 4-sulfo-3-{4'-bis-N,N-[β'-(β''-chloro-ethylsulfonyl)-ethyl-amino]-2'-chloro-1',3',5'-triazin-6'-ylamino}-phen-1-yl | chlorine | 2-SO$_3$H, 1-NH— phenyl | 4-{bis-N,N-[β-(β'-chloroethyl-sulfonyl)-ethyl]-amino}-2-chloro-1,3,5-triazin-6-yl | greenish blue (635) |
| 15 | 6-sulfo-3-{4'-bis-N,N-[β'-(β''-chloro-ethylsulfonyl)-ethyl-amino]-2'-chloro-1',3',5'-triazin-6'-ylamino}-phen-1-yl | chlorine | 4-HO$_3$S, 1-NH— phenyl | 4-{bis-N,N-[β-(β'-chloroethyl-sulfonyl)-ethyl]-amino}-2-chloro-1,3,5-triazin-6-yl | greenish blue (633) |
| 16 | hydrogen | hydrogen | covalent bond | 4-{bis-N,N-[β-(β'-chloroethyl-sulfonyl)-ethyl]-amino}-2-chloro-1,3,5-triazin-6-yl | reddish blue (569) |
| 17 | hydrogen | bromine | covalent bond | 4-{bis-N,N-[β-(β'-chloroethyl-sulfonyl)-ethyl]-amino}-2-chloro- | blue (580) |

-continued

| | Triphendioxazine compound (A) | | | | |
|---|---|---|---|---|---|
| Example | Radical $Z^0$ | Radical X | Radical A | Radical Z | Color shade |
| 18 | hydrogen | methyl | covalent bond | 4-{bis-N,N-[β-(β'-chloroethyl-sulfonyl)-ethyl]-amino}-2-chloro-1,3,5-triazin-6-yl | reddish blue |
| 19 | hydrogen | ethoxy-carbonyl | covalent bond | 4-{bis-N,N-[β-(β'-chloroethyl-sulfonyl)-ethyl]-amino}-2-chloro-1,3,5-triazin-6-yl | blue (570) |
| 20 | hydrogen | phenyl | covalent bond | 4-{bis-N,N-[β-(β'-chloroethyl-sulfonyl)-ethyl]-amino}-2-chloro-1,3,5-triazin-6-yl | violet (561) |
| 21 | hydrogen | phenoxy | covalent bond | 4-{bis-N,N-[β-(β'-chloroethyl-sulfonyl)-ethyl]-amino}-2-chloro-1,3,5-triazin-6-yl | blue (571) |
| 22 | hydrogen | methoxy | covalent bond | 4-{bis-N,N-[β-(β'-chloroethyl-sulfonyl)-ethyl]-amino}-2-chloro-1,3,5-triazin-6-yl | blue (569) |
| 23 | hydrogen | chlorine | —(CH$_2$)$_2$—NH— | 4-{bis-N,N-[β-(β'-chloroethyl-sulfonyl)-ethyl]-amino}-2-chloro-1,3,5-triazin-6-yl | blue (600) |
| 24 | hydrogen | chlorine | —(CH$_2$)$_2$—NH— | 4-{bis-N,N-[γ-(β'-chloroethylsulfonyl)-propyl]-amino}-2-chloro-1,3,5-triazin-6-yl | blue (601) |
| 25 | 4-{bis-N,N-[γ-(β'-chloroethyl-sulfonyl)-propyl]-amino}-2-chloro-1,3,5-triazin-6-yl | chlorine | covalent bond | 4-{bis-N,N-[γ-(β'-chloroethylsulfonyl)-propyl]-amino}-2-chloro-1,3,5-triazin-6-yl | reddish blue (560) |
| 26 | hydrogen | chlorine | —(CH$_2$)$_3$—NH— | 4-{bis-N,N-[β-(β'-chloroethylsulfonyl)-ethyl]-amino}-2-chloro-1,3,5-triazin-6-yl | blue (598) |
| 27 | hydrogen | chlorine | —(CH$_2$)$_3$—NH— | 4-{bis-N,N-[γ-(β'-chloroethylsulfonyl)-propyl]-amino}-2-chloro-1,3,5-triazin-6-yl | blue (600) |

I claim:

1. A triphendioxazine compound of the formula (1)

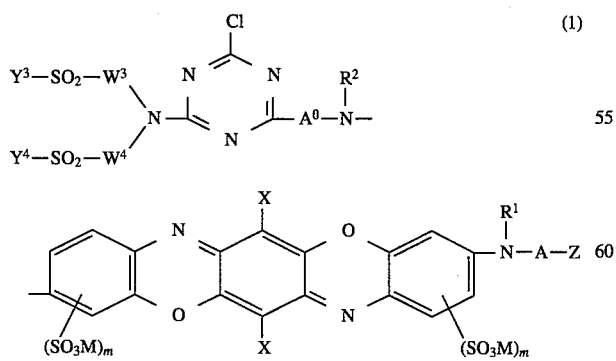

in which

M is hydrogen or an alkali metal;

m is the number 1 or 2;

X is hydrogen, halogen, optionally substituted alkyl having 1 to 4 carbon atoms, optionally substituted aryl, optionally substituted aryloxy, cyano, alkoxycarbonyl having 2 to 5 carbon atoms, aryloxycarbonyl, aminocarbonyl, N-alkyl-amino-carbonyl with an alkyl having 1 to 4 carbon atoms, N,N-dialkyl-aminocarbonyl with alkyls each having 1 to 4 carbon atoms, optionally substituted alkylcarbonyl having 2 to 5 carbon atoms, or optionally substituted arylcarbonyl;

$R^1$ is hydrogen, optionally substituted alkyl having 1 to 6 carbon atoms or optionally substituted aryl;

$R^2$ has one of the meanings given for $R^1$;

Z is a radical of the formula (2)

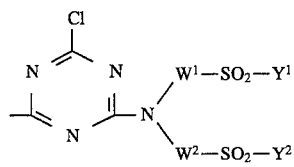

$Y^1$ is vinyl or is ethyl which contains a substituent in the β-position which can be eliminated by means of alkali to form the vinyl group, or is β-hydroxyethyl, $Y^2$ has one of the meanings of $Y^1$, with the proviso that $Y^1$ and $Y^2$ are not simultaneously β-hydroxyethyl, and with the proviso that both $Y^1$ and $Y^2$ are not simultaneously β-sulfatoethyl $W^1$ is alkylene having 2 to 6 carbon atoms, and $W^2$ has one of the meanings given for $W^1$;

A is a covalent bond or a group of the formula (3a)

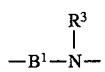 (3a)

in which $R^3$ has one of the meanings given above for $R^1$ and $B^1$ is alkylene having 2 to 6 carbon atoms or a alkylene having 3 to 10 carbon atoms which is interrupted by 1 or 2 hetero groups selected from groups of the formulae —O—, —NH—, —S—, —SO$_2$—, —CO—, —NH—CO—, —NH—SO$_2$—, —SO$_2$—NH—, —CO—NH—, —NH—CO—NH—, —NH—CO—O—, —CO—O—, —O—OC—NH—, —O—OC— and —N(R)—, where R is alkyl having 1 to 4 carbon atoms, or is cycloakylene having 5 to 8 carbon atoms, or is a groups of the formula phen, naphth, alk-phen, phen-alk, naphth-alk, alk-naphth, phen-alk-phen, alk-phen-alk, phen-D-phen, alk-D-phen, phen-D-alk, cy-alk, alk-cy, cy-alk-cy or alk-cy-alk, in which phen is phenylene unsubstituted or substituted by 1 or 2 substituents from the group consisting of methyl, ethyl, methoxy, sulfo and carboxy, naphth is naphthylene unsubstituted or substituted by 1 or 2 sulfo groups, alk is alkylene having 1to 6 carbon atoms unsubstituted or substituted by 1 or 2 substituents from the group consisting of hydroxyl, acetyloxy, sulfo, carboxy and sulfato and/or is interrupted by one of the hetero group selected from the group consisting of —O—, —NH—, —S—, —SO$_2$—, —CO—, —NH—CO—, —NH—SO$_2$—, —SO$_2$—NH—, —CO—NH—, —NH—CO—NH—, —NH—CO—O—, —CO—O—, —O—OC—NH—, —O—OC— and —N(R)—, cy is cycloalkylene having 5 to 8 carbon atoms, and D is a hetero group selected from the group consisting of —O—, —NH—, —S—, —SO$_2$—, —CO—, —NH—CO—, —NH—SO$_2$—, —SO$_2$—NH—, —CO—NH—, —NH—CO—NH—, —NH—CO—O—, —CO—O—, —O—OC—NH—, —O—OC— and —N(R)—, or the group —N(R$^1$)—B$^1$—N(R$^3$)— in total is a bivalent saturated heterocyclic radical; and $Y^3$ and $Y^4$ have one of the meanings given above for $Y^1$;

$W^3$ and $W^4$ have one of the meanings given above for $W^1$; and $A^0$ is a covalent bond or a radical of the formula (3b)

 (3b)

in which $R^4$ has one of the meanings given above for $R^1$ and $B^2$ has one of the meanings given above for $B^1$, or the group —N(R$^4$)—B$^2$—N(R$^2$)— is a bivalent saturated heterocyclic radical.

2. A compound as claimed in claim 1, in which m is the number 1.

3. A compound as claimed in claim 1, in which each X is chlorine.

4. A compound as claimed in claim 1, in which $W^1$, $W_2$, $W^3$ and $W^4$ are identical to one another or different form one another and each is ethylene or propylene.

5. A compound as claimed in claim 1, in which $Y^1$, $Y^2$, $Y^3$ and $Y^4$ are identical to one another or different from one another and each is β-chloroethyl or vinyl.

6. A compound as claimed in claim 1, in which $R^1$, $R^2$, $R^3$ and $R^4$ are each hydrogen.

7. A compound as claimed in claim 1 of the formula (1B)

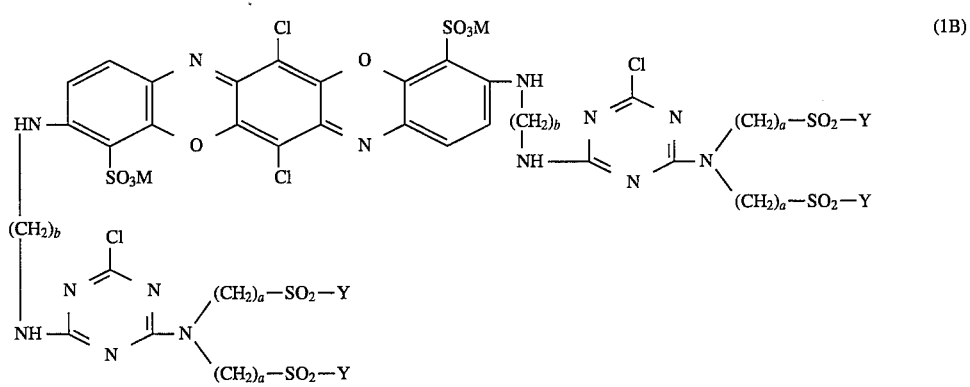 (1B)

in which M has the meaning given in claim 1, as is the number 2 or 3, b is the number 2 or 3 and Y is β-chloroethyl or vinyl.

8. A compound as claimed in claim 1 of the formula (1D)

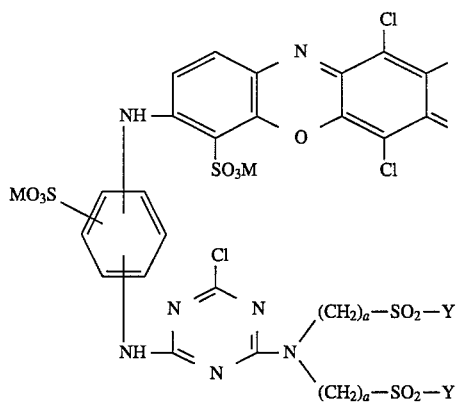
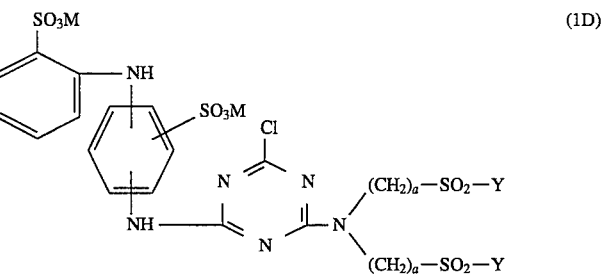

(1D)

in which M has the meaning given in claim 1, a is the number 2 or 3 and Y is β-chloroethyl or vinyl.

9. A method for dyeing a material containing hydroxy or carboxamide groups or both, in which a dyestuff is brought into contact with the material in an aqueous medium and fixing of the dyestuff on the material is carried out by means of heat or with the aid of an alkaline agent or with the aid of both measures, which comprises employing as the dyestuff a triphendioxazine compound of the formula (1) of claim 1.

10. A method according to claim 9, wherein the material is fiber-material.

11. A method as claimed in claim 9, wherein the process for dyeing is an exhaustion dyeing process and the dye liquor has an electrolyte salt content of less that than 50 g/l of dye liquor in total.

* * * * *